United States Patent [19]

Downey et al.

[11] Patent Number: 5,573,772
[45] Date of Patent: *Nov. 12, 1996

[54] METHODS FOR PROTECTING TISSUES AND ORGANS FROM ISCHEMIC DAMAGE

[75] Inventors: James M. Downey, Mobile, Ala.; Kevin M. Mullane, Del Mar, Calif.

[73] Assignees: Gensia, Inc., San Diego, Calif.; South Alabama Medical Science Foundation, Mobile, Ala.

[ * ] Notice: The term of this patent shall not extend beyond the expiration date of Pat. No. 5,443,836.

[21] Appl. No.: 214,942

[22] Filed: Mar. 17, 1994

Related U.S. Application Data

[63] Continuation-in-part of PCT/US94/02854 filed Mar. 15, 1994 which is a continuation-in-part of Ser. No. 33,310, Mar. 15, 1993, Pat. No. 5,443,836.

[51] Int. Cl.$^6$ .............................. A61F 2/02; A61K 9/48; A61K 9/20; A61K 9/14
[52] U.S. Cl. .......................... 424/423; 424/451; 424/464; 424/489; 514/936; 604/51
[58] Field of Search ..................... 424/423, 451, 424/464, 489; 514/936; 604/51

[56] References Cited

U.S. PATENT DOCUMENTS 3,868,451   2/1975   Stein et al. ................. 514/46

FOREIGN PATENT DOCUMENTS 0322242   6/1989   European Pat. Off. .
9406438   3/1994   WIPO .

OTHER PUBLICATIONS

Zhou et al., "Molecular Cloning and Characterization of an Adenosine Receptor: The A3 Adenosine Receptor". *Proc Nat Acad Sci U.S.A.* 1992; 89: 7432–7436.

Downey, J. M., Ischemic Preconditioning. Nature's Own Cardioprotective Intervention. *TCM* 1992; 2:170–176.

Liu, Y. and Downey, J. M., Ischemic Preconditioning Protects Against Infarction in Rat Heart. *Am. J. Physiol.* 1992; 263:H1107–H1112.

Liu, G. S. et al., Protection Against Infarction Afforded by Preconditioning is Mediated by A1 Adenosine Receptors in Rabbit Heart. *Circulation* 1991; 84:350–356.

Olsson, R. A. and Pearson, J. D., Cardiovascular Purinoceptors. *Physiol. Rev.* 1990; 70:761–845.

Downey, J. M. et al., Adenosine and the Anti–Infarct Effects of Preconditioning. *Cardiovascular Research* 1993; 27:3–8.

Thornton, J. D. et al., Intravenous Pretreatment with A1–Selective Adenosine Analogues Protects the Heart Against Infarction. *Circulation*, 1992; 85:659–665.

Zhou, Q. Y. et al., Molecular Cloning and Characterization of an Adenosine Receptor: The A3 Adenosine Receptor. *Proc. Natl. Acad. Sci. U.S.A.* 1992; 89:7432–7436.

(List continued on next page.)

*Primary Examiner*—Carlos Azpuru
*Attorney, Agent, or Firm*—Lyon & Lyon

[57] ABSTRACT

Methods for protecting tissues and organs including the heart central nervous system, and kidney from ischemic damage are described and claimed based upon the recognition that protection against infarction is mediated by A3 rather than A1 adenosine receptors, as was previously thought, and that the receptor mediating protection in other organs and tissues has not been defined. Methods for selectively stimulating A3 adenosine receptors are described and claimed, as such selection is shown to prevent or substantially reduce cell death resulting from ischemia with or without reperfusion in humans. According to this invention, the A3 adenosine receptor is selectively stimulated by administering a compound which is an A3 adenosine receptor-selective agonist. Prevention of tissue death is also achieved by administering a compound which is a non-selective adenosine receptor agonist together with compounds that act as antagonists to the A1 and A2 adenosine receptor.

35 Claims, 4 Drawing Sheets

OTHER PUBLICATIONS

Van Bergen, A. J. et al., A3 Receptors: Structure–Activity Relationships and Molecular Modeling, *MEDI*, 217 (1993).

Jacobson, R. A. et al., $N^6$–Benzyladenosine 5'–Uronamides: Selective Agonists for $A_3$ Receptors, *MEDI*, 244 (1994).

Gallo–Rodriguez, C. et al., Structure–Activity Relationships of $N^6$–Benzyladenosine–5'–Uronamides as A3–Selective Adenosine Agonists, *J. Med. Chem.*, 1994; 37:636–646.

Jacobson, K. A., Adenosine Receptors: Pharmacology, Structure–Activity Relationships, and Therapeutic Potential. *J. Med. Chem.* 1992; 35:407–422.

Walsh, R. S. et al., Role of Adenosine Receptor Subtypes in Preconditioning. *JACC* 1993; 21:116A.

Downey, J. M., Cardioprotective Role of A1 Receptor Ligands. *J. Mol. Cell Cardiol.* 1992; Y24:S.32.

Daly, J. W., Adenosine Receptors Targets for Future Drugs. *J. Med. Chem.* 1982; 25:197–207.

Anand, I. et al., Cardiovascular and Neurohormonal Effects of SDZ WAG 994, a Selective Adenosine Al Receptor Agonist, in Man. *JACC* 1995; 723–4:127A.

Gardner, C. J. et al., The Effects of GR79236 on Plasma Fatty Acid Concentrations, Heart Rate and Blood Pressure in the Conscious Rat. *Eur. J. of Pharmacol.* 1994; 257:117–121.

Salvatore, C. A. et al., Molecular Cloning and Characterization of the Human $A_3$ Adenosine Receptor, *Proc. Natl. Acad. Sci. USA*, 1993; 90:10365–10369.

Linden, J. et al., Molecular Cloning and Functional Expression of a Sheep $A_3$ Adenosine Receptor with Widespread Tissue Distribution, *Molecular Pharmacol.*, 1993; 44:524–532.

\* p < 0.05 vs. Vehicle: ANOVA with Scheffe's post-hoc test
\# p < 0.0005 vs. Vehicle: AVOVA with Scheffe's post-hoc test

METHODS FOR PROTECTING TISSUES AND ORGANS FROM ISCHEMIC DAMAGE

CROSS-REFERENCE TO RELATED APPLICATIONS

This application is a continuation-in-part of PCT/US94/02854, filed Mar. 15, 1994 which is a continuation-in-part of U.S. patent application Ser. No. 08/033,310, filed Mar. 15, 1993, now U.S. Pat. No. 5,443,836; the disclosures of this application are incorporated herein.

TECHNICAL FIELD

The present invention relates to methods of administering compounds to tissue to protect organs, such as the heart, the brain or the kidney, from ischemic injury, infarction, bradycardia, fibrillation, stunning, A-V conduction delays and other disorders. Specifically, the compounds administered to protect the organ selectively activate A3 adenosine receptors.

BACKGROUND OF THE INVENTION

In the United States, diseases caused by ischemia such as heart disease continue to be a major health problem. One type of disease results in the interruption of nutritional blood flow to the heart, brain or kidney tissue from blockage of a major coronary artery. Although blood flow can often be restored with thrombolytic treatment, it is usually administered too late to prevent irreversible damage. Moreover, the restoration of blood flow also can result in reperfusion injury, where the ultimate degree of tissue damage is greater than would be expected, if the reintroduction of blood and nutrients arrested all damage.

For example, of the 1.5 million people each year who suffer myocardial ischemia (the interruption of coronary blood flow), approximately 700,000 who survive myocardial ischemia that have myocardial infarction (dead heart tissue). For those people who survive with a myocardial infarction, the ischemic damage can form the basis for cardiac arrhythmias, such as bradycardia (abnormally slow heart beats), tachycardia (abnormally fast heart beats) and fibrillation (disorganized heart rhythms wherein the heart quivers rather than beats). About 400,000 people die each year from cardiac arrhythmias.

Protection against infarction has become a long-term goal of cardiology, because infarcted heart muscle cannot be regenerated and is a deficit that the patient must contend with for the remainder of his or her life; therefore a therapy which would cause the heart to better tolerate a period of ischemia is greatly desired. Such a therapy could increase the possibility that timely restoration of the coronary blood flow would salvage myocardial tissue. Such a therapy could also reduce the damage in an area of permanent occlusion. Although many drugs have been proposed to protect the ischemic myocardium, such as beta-blockers, free-radical scavengers, and calcium antagonists, virtually all have performed poorly in whole animal models. Therefore, methods and compounds are needed to both prevent and reduce the damage from ischemic events.

Interestingly, ischemia can be protective as well as injurious and methods for ischemic preconditioning of organs, such as the heart, brain or kidney have been described recently. Ischemic preconditioning refers to a phenomenon whereby a brief period of ischemia renders the myocardium very resistant to infarction from a subsequent schemic insult. [Downey, J. M.: Ischemic preconditioning. Nature's Own Cardioprotective Intervention. TCM 1992; 2:170–176.] The use of this ischemic preconditioning technique consists, in the case of the heart, of interrupting the blood flow through the coronary artery to the heart muscle for five minutes by coronary branch occlusion, followed by reperfusion, or restoring blood flow to the heart, for ten minutes. If the coronary blood flow is restored after five minutes of ischemia, not only will the heart fully recover with no cell death, but the heart will become very resistant to infarction from any subsequent ischemic insult. [See e.g., Liu, Y. and Downey, J. M. Ischemic preconditioning protects against infarction in rat heart. Am J Physiol 1992; 263:H1107–H1112.] Although ischemic preconditioning appears to be universally accepted as a powerful cardioprotectant, it is obviously not the type of intervention that could be administered to the acute myocardial infarction patient.

While the exact mechanism for ischemic preconditioning is not known, as a result of testing in various animal models, ischemic preconditioning appears to be mediated by adenosine which is released during the short ischemic event and populates the adenosine receptors. [Liu, G. S., et al.: Protection against infarction afforded by preconditioning is mediated by A1 adenosine receptors in rabbit heart. *Circulation* 1991; 84:350–356.] Previously, two types of adenosine receptors have been described, specifically the A1 and A2 adenosine receptors. [Olsson, R. A., Pearson, J. D.: Cardiovascular purinoceptors. Physiol Rev 1990; 70:761–845.] In myocardium, stimulation of A1 adenosine receptors is associated with bradycardia and constricts blood vessels, while A2 receptors mediate coronary vasodilation and inhibit neutrophil activation. Virtually all previous work has indicated that only the A1 adenosine receptor is involved in initiating the preconditioning protection. [See e.g., Downey, J. M., et al., Adenosine and the anti-infarct effects of preconditioning. *Cardiovascular Research* 1993; 27:3–8.] The A2 adenosine receptor has not been implicated.

As a prospective preconditioning compound, adenosine has been investigated, but the problems associated with administering adenosine outweigh the myocardial benefits. While adenosine does possess ischemic protective abilities, it can only be administered by selective infusion into the coronary artery, as an intravenous injection would cause too much hypotension at doses required for ischemic preconditioning. [Downey, J. M., et al., Adenosine and the anti-infarct effects of preconditioning. *Cardiovascular Research* 1993; 27:3–8.] Also, increasing evidence exists that adenosine is a mediator of the sensation of anginal pain. Furthermore, adenosine is extremely labile in blood with a half-life of only seconds. [Moser, G. H., et al., Turnover of adenosine in plasma of human and dog. *Am J Physiol* 1989; 256:C799–C806.] Thus, adenosine is an unlikely candidate for medical treatment of acute myocardial infarction or as a infarction prevention drug.

Adenosine analogues which are capable of selectively activating the A1 adenosine receptor (A1-selective agonists) also have been investigated. Although adenosine analogues which are the A1-selective agonists, such as $N^6$-(phenyl-2R-isopropyl)-adenosine (R-PIA) and 2-chloro-$N^6$-cyclopentyladenosine (CCPA), have been shown to provide beneficial ischemic preconditioning effects when intercoronarily infused before an ischemic insult, undesirable side effects from activation of the A1 adenosine receptor, e.g. hypotension, A-V conduction delays, bradycardia, narcosis, bronchial spasm, negative inotropic activity and renal vasoconstriction, may present an insurmountable obstacle to achieving a practical therapy based on parenteral administration of A1-selective agonists. [See e.g., Thornton, J. D., et al., Intravenous Pretreatment With A1-Selective Adenosine Analogues Protects the Heart Against Infarction. *Circulation*, 1992; 85:659–665.]

Recently, a third adenosine receptor, the A3, has been characterized. [Zhou, Q. Y., et al., Molecular cloning and characterization of an adenosine receptor: The A3 adenosine receptor. *Proc Natl Acad Sci* 1992; 89:7432–7436.] It is reported that the A3 adenosine receptor cloned from rat brain, designated R226, shares high sequence identity with the two previously identified adenosine receptors. R226 has been reported to bind the non-selective adenosine agonists N-ethyladenosine 5'-uronic acid (NECA), and the A1-selective agonist $N^6$-2-(4-amino-3-iodophenyl)-ethyladenosine (I-APNEA), but not to bind the A1-selective antagonists 1,3 dipropyl-8-cyclopentylxanthine (DPCPX) and 8-{4-[({[(2-aminoethyl)amino]carbonyl}methyl)oxyl-phenyl}-1,3-dipropylxanthine (XAC). Nothing has been currently reported about its physiological role.

Firestein, et al., U.S. patent application Ser. No. 08/070,689, now abandoned, describes DNA encoding Human adenosine A3 receptor, isolated human A3 receptor, cells expressing the same and uses thereof.

Andrew J. van Bergen, et al., *Abstracts of Papers*, 206th National Meeting of the American Chemical Society, Chicago, Ill., 1993, MEDI 217, proposed a preliminary structure activity relationship for some A3 receptor agents. Further, Kenneth A. Jacobson, et al., *Abstracts of Papers*, 207th National Meeting of the American Chemical Society, San Diego, Calif., 1994, MEDI 244, reported N6-benzyladenosine 5'-uronamides as selective agonists for rat brain A3 receptor. This work was also published in expanded form as "Structure-Activity Relationships of $N^6$-Benzyladenosine-5'-uronamides as A3-Selective Adenosine Agonists" in J. Med. Chem., 37, 636 (1994).

Christopher Salavatore, et al., Proc. Natl. Acad. Sci. USA 90 (1993) reported the binding constants for several agents to the human A3 adenosine receptor.

Joel Link, et al., Mol. Pharmacol. 44:524–532 (1993) also proposed a preliminary structure activity relationship for binding of some A3 receptor agents to recombinant sheep A3 adenosine receptor.

SUMMARY OF THE INVENTION

The present invention relates to the discovery that the A3 adenosine receptor is the mediator of ischemic preconditioning, and selective activation of the A3 adenosine receptor renders organs such as the myocardium resistant to subsequent ischemic insults without negative side effects such as heart block or hypotension. Ischemic preconditioning can be mimicked by administering compounds which selectively activate the A3 adenosine receptor.

Thus, one aspect of the present invention relates to methods for preconditioning organs such as the heart, brain or kidney by administering a molecule which is an A3 adenosine receptor-selective agonist. This method has the advantage of providing protection to myocardial tissue in the event a subsequent ischemic insult occurs without causing the unwanted side effects inherent to activation of the A1 adenosine receptor. Therefore it is an aspect of the present invention to provide protection without causing unwanted side effects such as heart block, bradycardia or significant hypotension.

In another aspect, the present invention relates to a method for selectively activating the A3 adenosine receptor by administering an agonist to the A3 adenosine receptor together with an antagonist to the A1 adenosine receptor, thereby ensuring the prevention of any unwanted A1 stimulation side effects.

In another aspect, the present invention relates to a method for selectively activating the A3 adenosine receptor by administering an agonist to the A3 adenosine receptor together with a molecule that is an antagonist to the A1 adenosine receptor and with an antagonist to the A2 adenosine receptor. This method does not require the A3 agonist to be specific to A3 only and also ensures against provoking any unwanted A2 stimulation side effects.

In one preferred embodiment, the present invention relates to methods of administering compounds which selectively stimulate the A3 adenosine receptor and thereby prevent ischemic injury during surgery. Such compounds may be administered orally or preferably intravenously prior and/or during surgery.

In another preferred embodiment, the present invention relates to methods for administering compounds which selectively stimulate the A3 adenosine receptor to prevent further ischemic injury after acute myocardial infarction has occurred. Such compounds could be administered orally or preferably intravenously. Alternatively such compounds might be orally administered in a prophylactic manner to high-risk patients, i.e., those at high risk of heart attack due, for example, to previous attacks or to atherosclerosis or to pending surgery.

The invention further involves the identification of patients in need of treatment who are at risk for adverse clinical outcomes, including adverse cardiovascular and adverse cerebrovascular events. Risk factors for those patients undergoing cardiac surgery include elevated age (for example, above 65 years of age); emergency or urgent surgery which may be complicated by unstable angina; failed percutaneous transluminal coronary angioplasty; decreased left ventricular function (as determined by an ejection fraction of less than 40%); chronic or acute renal failure; dysrhythmia (under treatment); or myocardial infarction within the past several years. See, e.g., Manango, Anesthesiology 72:153–84 (1990). Risk factors for those patients undergoing non-cardiac surgery include advanced age (for example 65–70 years of age); atherosclerotic heart disease, i.e., coronary artery disease, as evidenced by peripheral vascular disease or carotid artery disease; diabetes; renal failure; heart failure under therapy; left ventricular hypertrophy and hypertension; hypertension for over five years; emergency or urgent surgery; myocardial infarction within six months to one year prior to surgery; angina; arrhythmia or hypercholesterolemia. The invention also includes identification of patients in need of prophylactic administration of an A3 agonist because of a chronic, genetic or similar condition or due to angina, transient ischemia attack, evolving or recent myocardial infarction, or evolving or recent stroke.

In another preferred embodiment, the present invention relates to methods for administering compounds which selectively stimulate the A3 adenosine receptor as a program for continual preconditioning. This method would provide the advantage of maintaining the heart or other organ in a preconditioned state indefinitely and would be appropriate for patients who are at high risk of myocardial infarction, thereby allowing them to better tolerate an ischemic event. Preferably, such treatment would involve the intermittent administration of the agonist, as continual administration of a receptor agonist may result in the undesired side effects of down regulation of the receptor or of tolerance.

Another preferred embodiment of the present invention is the use of a specific adenosine A3 agonist. The specificity of said agonist is defined by having a ratio of A3 receptor affinity versus A1 and/or A2 receptor affinity of at least about 10 to 1 and more preferably about 100 to 1.

Other aspects, advantages and embodiments of the invention will be apparent from the following description of the preferred embodiments, the figures and from the claims.

DETAILED DESCRIPTION OF THE PREFERRED EMBODIMENT

Figure 1:
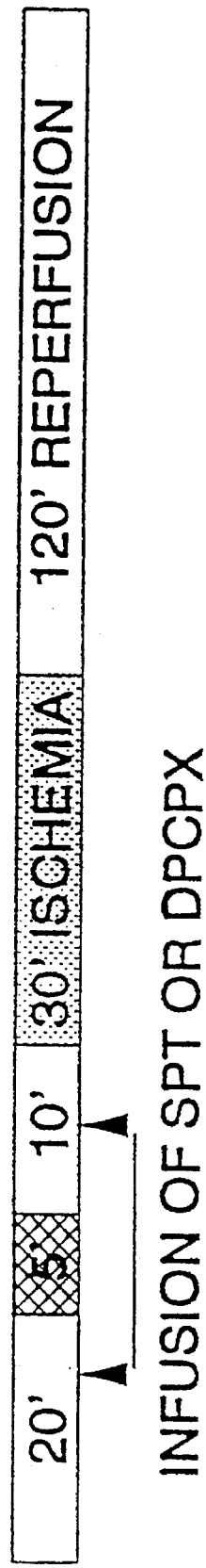
FIG. 1 is a depiction of the experimental protocol used to screen compounds for preconditioning the heart.

The present invention provides novel methods for preconditioning organs such as the heart, brain or kidney to prevent or reduce tissue damage, if the organ experiences an ischemic insult. These methods are based upon the recognition that selective stimulation or activation of the A3 adenosine receptor provides beneficial preconditioning effects which prevent or reduce damage to tissue from an ischemic insult. Selective stimulation of the A3 adenosine receptor also will maximize desired protective benefits, while minimizing unwanted side effects from the stimulation of the A1 and A2 adenosine receptors, such as heart block or hypotension. Therefore, methods and compounds are described and claimed which will promote selective stimulation of the A3 adenosine receptor.

The term "preconditioning" refers to the treatment of an organ before, during or after an ischemic event. Although the term encompasses the prophylactic treatment of an organ considered at risk of such an event, it is not intended to limit treatment only in advance of the event.

The term "receptor" refers to a macromolecule capable of recognizing and selectively binding with a ligand, and which after binding the ligand, is capable of generating a physical or chemical signal that initiates the chain of events leading to the physiological response. [Blecher, M., et al., *Receptors and Human Disease.* Williams & Wilkins, Baltimore, 1981, Chapter 1.] Adenosine receptors are proteins found in animals and humans which can bind the ligand, adenosine, causing a physiological response. Adenosine receptors have been located in a variety of tissues and cells, including hippocampus, adipocytes, atrioventricle node, striatum, platelets, neutrophils, coronary vasculature and olfactory tubercule. [Jacobson, K. A., Adenosine Receptors: Pharmacology, Structure-Activity Relationships, and Therapeutic Potential. *J Med Chem,* 1992; 35:407–422.]

Ligands which bind to the adenosine receptor, thereby generating a physiological response which mimics the response caused by the adenosine receptor binding adenosine, are termed adenosine receptor agonists. Likewise, ligands which bind to the adenosine receptor causing the inhibition of the adenosine receptor physiological response are termed adenosine receptor antagonists. Several agonists and antagonists to the A1 and A2 adenosine receptors have been identified; some of these compounds are listed in Table 1.

Preferably, stimulation or activation of the A3 adenosine receptor occurs exclusive of stimulation or activation of the A1 and A2 adenosine receptors. Since identification of ligands which can selectively stimulate or activate the A3 adenosine receptor is an important aspect of the present invention, methods for screening compounds to determine the beneficial preconditioning effects from selectively stimulating the A3 adenosine receptor are provided as described in Example 1 given below. As used herein, useful agonists to the adenosine A3 receptor will have a selectivity for the A3 receptor relative to A1 and/or A2 receptors of at least 10:1 and preferably of about 100:1. The ratio may be determined by relative binding potencies at the A1, A2 and A3 adenosine receptor binding sites using methods known in the art. Currently several potent and selective agonists of the A3 receptor are known. These include but are not limited to $N^6$-2-(4-amino-3-iodophenyl)ethyladenosine (I-APNEA), R-phenylisopropyladenosine (R-PIA), $N^6$-benzyladenosine-5'-N-ethyluronamide, 5'-N-ethylcarboxamidoadenosine (NECA), $N^6$-benzyladenosine-5'-N-methyluronamide, $N^6$-(3-bromobenzyl)adenosine-5'-N-methyluronamide, $N^6$-(3-iodobenzyl)adenosine-5'-N-methyluronamide, and $N^6$-(3-chlorobenzyl)adenosine-5'-N-methyluronamide. Other potent and selective A3 receptor agonists fall within the scope of the present invention.

UTILITY

The methods for protecting tissues and organs from ischemic damage of the present invention may be used in the treatment of a variety of human clinical situations. In particular, these compounds may be used in treating cardiovascular disorders in which injury or dysfunction is caused by ischemia and/or reperfusion (following a period of ischemia). These injuries or disfunctions include but are not limited to (1) heart attack, a situation that arises from obstruction of one or more of the coronary arteries supplying blood to the heart muscle, and which, if prolonged, leads to irreversible tissue damage; (2) angina pectoris, a clinical condition in which the blood supply to the heart is sufficient to meet the normal needs of the heart but insufficient when the needs of the heart increase (e.g. during exercise), and/or when the blood supply becomes more limited (e.g. during coronary artery spasm); (3) unstable angina associated with pain at rest; and (4) silent ischemia. Thus, a patient with acute myocardial infarction (undergoing a heart attack) would benefit from administration of an agent which activates the A3 adenosine receptor, thus limiting the amount of tissue damage. Likewise, patients undergoing procedures to re-open a blocked vessel, including thrombolysis, percutaneous transluminal coronary angioplasty (PTCA) or atherectomy procedures, also would benefit from treatment with the present invention to limit the deleterious effects of reperfusion. Further, patients with transient ischemic attacks or strokes who are treated with thrombolysis or carotid endarterectomy would benefit from treatment with the present invention as would patients undergoing revascularization procedures or thrombolysis to resolve stenotic lesions of renal arteries to alleviate hypertension and renal disfunction.

In advanced coronary artery disease or persistent chest pain at rest, a number of clinical procedures are currently used to improve blood supply to the heart. These include percutaneous transluminal coronary angioplasty (PTCA), percutaneous transluminal directional coronary atherectomy, laser atherectomy, intravascular stents and coronary artery bypass graft surgery. The methods and compounds of this invention will also be useful as adjunctive therapies to these techniques. Other clinical settings that involve ischemia would also be ameliorated by agents which improve ischemic tolerance including organ transplantation, skin flap grafting and other reconstructive surgery, peripheral vascular disease, sepsis, endotoxemia, hemorrhagic shock, pulmonary emboli, pulmonary injury secondary to burns (thermal injury) or septicemia, pulmonary hypertension, microembolization, glomerulonephritis or progressive glomerulosclerosis, atherosclerosis, myocarditis, vasculitis, cardiomyopathies, intestinal ischemia, peripheral vascular disease, transient ischemic attacks, stroke, head trauma and cardiopulmonary arrest.

As can be easily seen, methods for selectively activating the adenosine A3 receptor find widespread clinical utility without the side effects of other treatments. We have demonstrated that tissue may be protected from ischemic damage by activation of the adenosine A3 receptor as indicated in Example 1 in isolated rabbit hearts and in Example 2 in intact rabbits. Example 3 indicates that the preconditioning cardioprotective effect previously thought to be mediated by the A1 receptor is indeed mediated by activation of the A3 receptor. Example 4 describes the dose-response effect of activation of the A3 receptor by the agonist APNEA and shows a significant reduction of infarct size by this method of treatment. Finally Example 5 describes the applicants' A3 receptor binding assay. This method involves the use of the human A3 receptors which are the subject of pending U.S. patent application 08/070,689, now abandoned, which is incorporated herein by reference. The results of this A3 binding assay may be compared to the results of A1 and A2 binding assays known in the art to determine the selectivity and potency of potential A3 receptor agonists.

Other situations in which the method of the present invention would find utility are known to those skilled in the art and are not limited to those described above. For example, it is known in the art how to administer A3 agonists to treat organs other than the heart to protect other tissues from ischemic damage.

Formulations

Compounds of the invention are administered to the affected tissue at the rate of from 0.1 to 100 nmol/min/kg, preferably from 1 to 20 nmol/min/kg. Such rates are easily maintained when these compounds are intravenously administered as discussed below. When other methods are used (e.g., oral administration), use of time-release preparations to control the rate of release of the active ingredient may be preferred. These compounds are given in a dose of about 0.2 mg/kg/day to about 50 mg/kg/day, preferably from about 0.5 mg/kg/day to about 10 mg/kg/day, preferably given in intermittent periods, preferably with each period of treatment being 24 hours or less in order to avoid down regulation or tolerance.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection including perfusion, for example during CABG surgery, as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservative such as ethyl or n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 200 µmoles of active material compounded with an appropriate and convenient amount of carrier material which may vary from about 5 to about 95% of the total composition. It is preferred that pharmaceutical composition be prepared which provides easily measurable amounts for administration. For example, an aqueous solution intended for intravenous infusion should contain from about 20 to about 50 µmoles of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous with the compounds susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be sorted in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of an adenosine A3 receptor agonist compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

The method may be used following thrombolysis for coronary occlusion. The compound would be given as a sterile injectable preparation with water or isotonic sodium chloride as the solvent. The solution can be administered intravenously or directly into the coronary artery at the time of left heart catheterization or into a carotid artery. The rate of administration could vary from 1 to 20 nmole/min/kg with, for example, an infusion volume of 30 ml/hr. Duration of therapy would typically be about 96 hours.

Angina and early myocardial infarcts can be treated by intravenous administration using a sterile injectable preparation using the rates discussed above.

Capsules comprising adenosine A3 agonists suitable for oral administration according to the methods of the present invention may be prepared as follows: (1) for a 10,000 capsule preparation: 1500 g of adenosine A3 receptor agonist is blended with other ingredients (as described above) and filled into capsules which are suitable for administration depending on dose, from about 1 capsule per day to about 8 capsules per day (2 capsules per 6 hours), to an adult human.

The following examples are illustrative of the invention but they should not however be construed as specifically limiting the scope of the invention and variations of the invention, now known or later developed, are considered to fall within the scope of the present invention as herein after claimed.

EXAMPLE 1

Comparison of the Reduction of Infarct Size in Preconditioned Rabbits and Rabbits Treated with $A_3$ Agonist The following example addresses the effect of a variety of adenosinergic agents on infarct size induced by coronary artery occlusion and reperfusion in rabbits, and compares these effects to those elicited by ischemic preconditioning. Appropriate doses of the adenosinergic agents were established in a separate group of animals using hemodynamic endpoints to define pharmacological activity. Doses of adenosinergic agents thus defined were then employed in the setting of ischemia-reperfusion to evaluate cardioprotective efficacy.

Chemicals

Adenosine (ADO) was obtained from Sigma. 8-(p-Sulfophenyl)-theophylline (SPT) and 8-cyclopentyl-1,3-dipropylxanthine (DPCPX) were purchased from Research Biochemicals Inc., Natick, Mass. $N^6$-(2-(4-aminophenyl)ethyl) adenosine (APNEA) was provided by Dr. Ray A. Olsson, Department of Internal Medicine, the University of South Florida, Tampa, Fla.

For use in this experiment, ADO, CCPA and SPT were mixed with 1.0 ml of distilled water while DPCPX and APNEA were solubilized in ethanol and DMSO, respectively. These solutions were then diluted in Krebs buffer to the final concentration just before the experiments started.

Surgical Preparation of the Animals

New Zealand white rabbits of either sex, between 1.4–2.4 kg, were anesthetized with intravenous sodium pentobarbital (30 mg/kg). The neck was opened and a tracheotomy was performed. The rabbits were ventilated with 100% oxygen via a positive pressure respirator (MD industries, Mobile, Ala.). Ventilation rate was 30–35 breaths per minute, and tidal volume was approximately 15 ml. A left thoracotomy was performed in the fourth intercostal space and pericardium was opened to expose the heart. A 2-0 silk suture with an RB taper needle was passed around a branch of the left coronary artery, and the end of the silk were threaded through a small vinyl tube to form a snare. The heads were quickly excised and mounted on a Langendorff apparatus and perfused at constant pressure with Krebs buffer containing (in mM) 118.5 NaCl, 4.7 KCl, 1.2 $MgSO_4$, 1.2 $K_2PO_4$, 24.3 $NaHCO_3$, 2.5 $CaCl_2$ and 10 glucose. The Krebs buffer was gassed with 95% $O_2$ plus 5% $CO_2$ which resulted in a pH of 7.4–7.5 and $pO_2$ of 500–600 mm Hg. The temperature of the perfusate was maintained at 37° C. The perfusion pressure was kept at 75 mm Hg. Pacing electrodes were placed on the right atrium and all hearts were paced at 200 beats/minute with pulses of 5 volts and 4 msec duration to keep the heart rate constant. A fluid-filled latex balloon connected to a transducer via PE240 tubing was inserted into the left ventricle. Balloon volume was adjusted to set the left ventricular diastolic pressure at 10 mm Hg at the beginning of the experiment. Total coronary artery flow was measured by timed collection of buffer from the chamber into a graduated cylinder. Regional ischemia was effected by pulling the snare tight and clamping the tube with a hemostat. Global ischemia was performed by clamping the inflow tubing of the Langendorff apparatus. Reperfusion was achieved by releasing the restriction. All hearts were allowed to equilibrate for 20 minutes before the experiments were started. Heart rate (HR), coronary flow (CF) and left ventricular developed pressure (LVDP) were recorded at the point just before and at the end of each treatment with the pacing momentarily turned off.

Measurement of Infarct and Risk Area

For the group to be exposed to ischemia, the silk suture under the coronary branch was tightly tied to occlude the artery at the end of each experiment, and a 0.5% suspension of fluorescent particles (1–10 um diameter from Duke Scientific Corp., Palo Alto, Calif.) were infused into the perfusate to mark the risk zone as the non-fluorescent tissue. The hearts were removed from the Langendorff apparatus, weighed and then frozen. The hearts were cut into 2 mm transverse slices. The slices were thawed and incubated in 1% triphenyl tetrazolium chloride (TTC) in pH 7.4 buffer for 20 minutes at 37° C. TTC reacts with NADH and dehydrogenase enzymes and stains all tissue still having them to a deep red color. The infarcted area of the heart loses those constituents and does not stain. After staining, the area of infarcted tissue (TTC negative tissue) and the risk zone (area lacking fluorescence under ultraviolet light) in each slice were traced. The area of infarct and risk zone were determined by planimetry of the tracing. The volume of infarcted myocardium and myocardium at risk was then calculated by multiplying the planimetered areas by the slice thickness.

Experimental Protocols

The animals were divided into 10 groups. The basic protocol is shown in FIG. 1. The hearts in all groups were subjected to 30 minutes of coronary branch occlusion followed by 120 minutes of reperfusion. Control group (CON, n=10) only experienced the above-mentioned 30 minutes of regional ischemia while the preconditioned group (PC, n=12) received an additional 5 minutes of global ischemia plus 10 minutes of reperfusion prior to the 30 minute occlusion. In the adenosine group (ADO, n=6) and the APNEA group (APNEA, n=5), the hearts were exposed to 10 uM adenosine and 50 nM APNEA respectively, for 5 minutes as a substitute for ischemic preconditioning. The drug was allowed to washout for 10 minutes before the 30 minute ischemia was started. In groups receiving SPT, the blocker was included in the perfusate for 15 minutes at 100 uM starting 5 minutes before the exposure of ADO (ADO-SPT group, n=6) or APNEA (APNEA-SPT group, n=5) or 5 minutes before and after 5 minutes of preconditioning ischemia (PC-SPT group, n=5). Groups ADO-DPCPX (n=6), APNEA-DPCPX (n=4) and PC-DPCPX (n=5) were identical to three SPT groups except that 200 nM DPCPX was substituted for the SPT.

Statistics

All results are expressed as group mean±SEM. The differences among groups was determined by a one-way analysis of variance with a Newman-Keuls post hoc test. A value of $p<0.05$ was considered to be significant.

Data were contributed from 73 rabbits. No heart which was not perfused with buffer within one minute after excision or whose developed pressure was less than 80 mm Hg after equilibration was used in the present study.

Measurement of Effect of Agents on Hemodynamic Responses

In order to ensure that the adenosinergic agents were active at the concentrations employed, hemodynamic responses were measured in a separate group of animals who experienced similar surgery described above except the coronary snare was not installed and therefore the second group of animals were not exposed to ischemia. The hearts were quickly excised and mounted on the Langendorff apparatus and perfused with Krebs buffer. The depressant effect of adenosine on atrioventricular (AV) conduction time was measured at a constant rate of atrial pacing, as an index of A 1-mediated activity. A constant pacing atrial cycle length is necessary because AV conduction is modulated by atrial rate, which in turn is affected by adenosine. The hearts were electrically paced at an atrial cycle length of 300 ms (4 Hz, pulse duration of 2 ms) via bipolar electrode placed on the right atrium. Measurements of AV conduction time were made by a bipolar extracellular electrode on the surface of the hearts which then were connected with the EKG recorded. Stimulus-to-ventricle (S-R) interval was used from EKG as the measure of AV conduction. Coronary flow was measured with a flowmeter (BL-622, Biotronex), as an index of A2-mediated activity. Doses of antagonists were determined by their ability to block these hemodynamic effects of adenosine and adenosine agonists in the isolated heart. All drugs were infused into the perfusion line at various flow rates via a syringe pump to achieve the desired perfusate concentrations. Doses defined in this manner were then employed in studies on infarct size.

Discussion of Results

Figure 2:
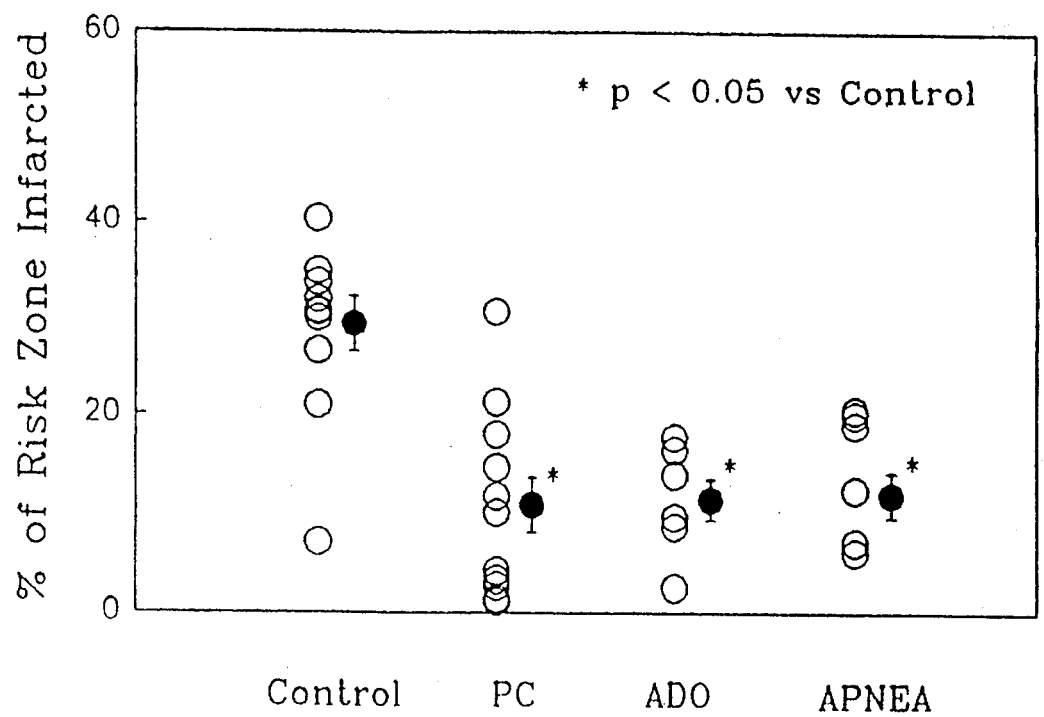
FIG. 2 is a graphical depiction of the comparison of the protective effects of ischemic, adenosine and APNEA preconditioning on the heart.

FIG. 2 summarizes the hemodynamic data for all groups. Heart rate (HR), coronary flow (CF) or left ventricular developed pressure (LVDP) at pretreatment from all groups was similar. Treatment with SPT or DPCPX alone only slightly affected hemodynamics in the hearts. However, infusing ADO (10 uM) for 5 minutes significantly decreased the HR from 176±8 beats/min to 149±6 beats/minutes and increased CF from 7.6±0.6 ml/g/min to 10.3±0.8 ml/g/min via A1 and A2 receptors, respectively. Those effects completely disappeared during the 10 minutes of washout. Both the HR decrease (A, effect) and CF increase (A2 effect) from ADO infusion could be abolished by SPT (100 uM), a non-selective antagonist. The highly selective A1 antagonist, DPCPX (200 nM), only eliminated the decrease in HR but did not affect the increase in CF. APNEA (50 nM), an A3 receptor agonist, did not significantly alter HR, CF or LVDP at this dose.

Figure 3:
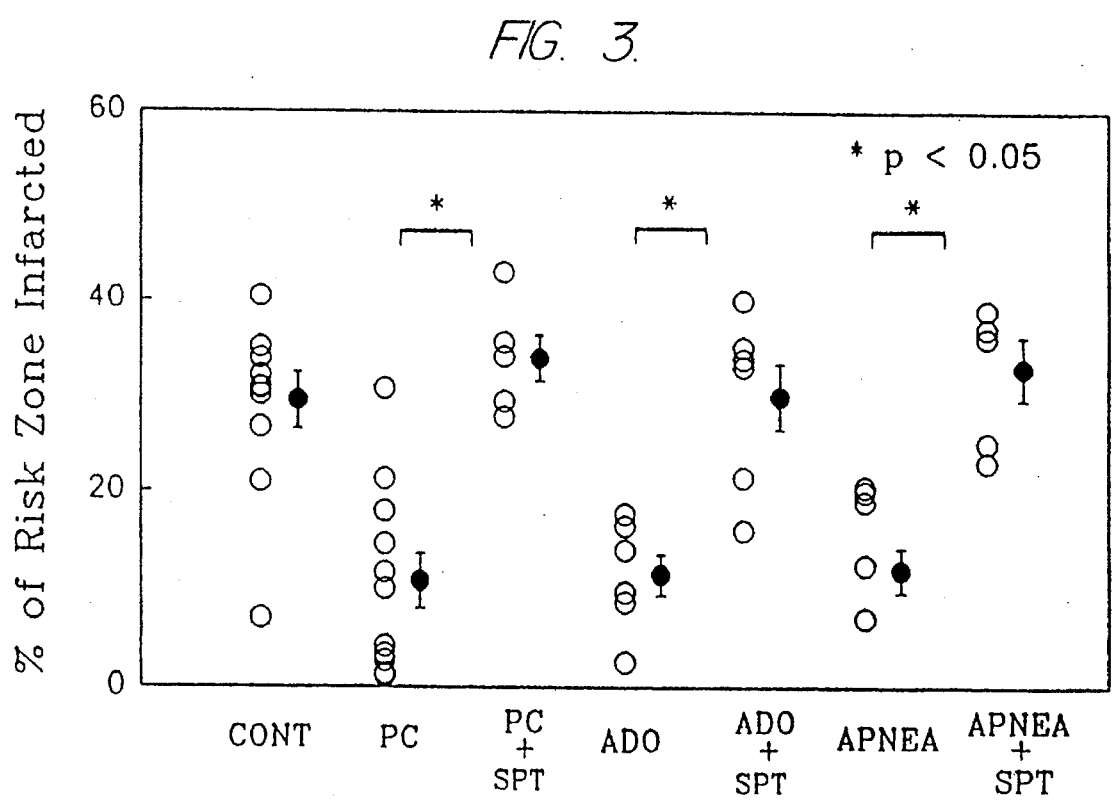
FIG. 3 is a graphical depiction of the comparison of the protective effects of ischemic, adenosine and APNEA preconditioning on the heart when 8-SPT is administered as an A1 adenosine receptor-selective antagonist.
Figure 4:
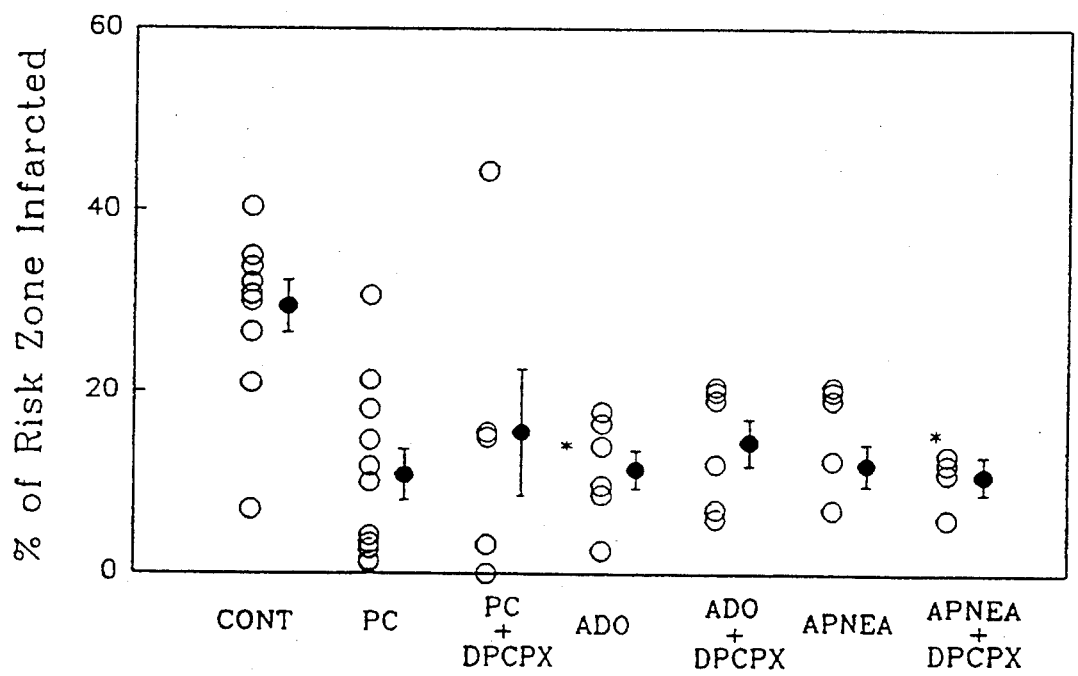
FIG. 4 is a graphical depiction of the comparison of the protective effects of ischemic, adenosine and APNEA preconditioning on the heart when DPCPX is administered as an A1 adenosine receptor-selective antagonist.

Infarct size data are shown in FIG. 3. There was no significant difference in the area at risk for all groups. Infarct size was normalized and expressed as percentage of the area at risk infarcted. In the isolated rabbit hearts, 30 minutes of coronary branch occlusion caused 29.4±2.9% of risk zone to be infarcted in control hearts while only 10.8±2.8% infarcted in hearts subjected to ischemic preconditioning ($p<0.01$). PC (preconditioning) protected the hearts from infarction as effectively as in previous studies in rabbits in vivo. Exposure to either ADO (10 uM) or APNEA (50 nM) for 5 minutes also protected the hearts (11.4±2.1% and 11.9±2.3%, respectively). Infarct sizes in the ADO and APNEA groups were not different from those in the preconditioned group and were significantly smaller than those in the control group ($p<0.01$) (FIG. 2). In the present study, however, SPT (a non-selective adenosine receptor antagonist) completely blocked protection against myocardial infarction from either PC (33.8±2.4%), exposure to ADO (29.8±3.4%) or APNEA (32.8±3.3%). DPCPX is a highly A1-selective and powerful adenosine receptor blocker. We found that DPCPX (200 nM) entirely blocked adenosine's effect on heart rate. However, in terms of the infarct size, DPCPX failed to prevent the protection against infarction afforded by PC (15.6±7.8%), or the infusion of either 10 uM ADO (14.4±7.0%) or APNEA (8.7±1.7%). (The infarct size in the three DPCPX groups (PC-DPCPX, ADO-DPCPX and APNEA-DPCPX) was not significantly different from the groups without DPCPX (PC, ADO and APNEA) (FIG. 4)).

Based upon the results presented, the applicants have now demonstrated that isolated buffer perfused rabbit hearts can be protected against infarction by ischemic preconditioning as well as by activation of the A3 adenosine receptor. The advantage of the isolated buffer perfused heart model is that it allows the delivery of drugs to the heart at a known dose and schedule. Studies with this model have led us to propose that preconditioning is mediated by the A3 adenosine receptor rather than the A1 as was previously thought.

These results indicate that neither the A1 nor A2 adenosine receptors are activated with 50 nM APNEA. Further, use of the A1-selection antagonist DPCPX (200 nM) completely blocked the reduction of heart rate, which is an A1 adenosine receptor mediated effect, but did not block the beneficial effects of APNEA.

EXAMPLE 2

The $A_3$-receptor mediates the cardioprotective effect of I-APNEA in the intact rabbit.

The previous studies have demonstrated that the cardioprotective effects of APNEA in isolated rabbit hearts is not prevented by the selective A1-receptor antagonist, DPCPX. No studies have demonstrated the same result in the intact, blood perfused heart. In this study, the effect of the adenosine receptor agonist, I-APNEA, on infarct size in the anesthetized rabbit was compared to the protection observed with ischemic preconditioning (PC).

New Zealand White rabbits (1.5–2.5 kg) were anaesthetized with pentobarbital sodium (40 mg/kg) administered via a catheter in a marginal ear vein. The animals were intubated with a pediatric cuffed endotracheal tube and ventilated with room air using a positive pressure respirator (Harvard Apparatus, Natick, Mass.). The heart was exposed in situ via an incision between the left 4th and 5th ribs, and a branch of the left coronary artery was isolated, using a 3-0 silk suture on RB-taper needle, for later ligation to induce 30 minutes of ischemia followed by 180 minutes of reperfusion. A catheter inserted into a femoral vein was used for administration of fluids and drugs. Infarct size was measured using the method described in the section entitled "Measurement of Infarct Size and Risk Area" in Example 1.

All animals received 30 minutes of regional ischemia, induced by tightening the suture placed around the coronary artery. Following the 30 minutes of ischemia, the suture was loosened, and reperfusion was allowed for the ensuing 180 minutes. Control animals received only the 30 minutes of ischemia and 180 minutes of reperfusion (n=9). Ischemic preconditioning (PC) was induced by 5 minutes of occlusion of the coronary artery followed by 10 minutes of reperfusion before the 30 minutes of occlusion (n=7). In a separate group of rabbits, I-APNEA was delivered intravenously as a slow bolus injection (0.25 mg/kg), beginning 15 minutes prior to the 30 minutes occlusion (n=8). In two additional groups of rabbits, the effects of the A1-selective adenosine receptor blocker, DPCPX, were tested against the effects of PC (n=6) and I-APNEA (n=8). In these animals, DPCPX was administered as a slow bolus (5 minutes) injection (0.5 mg/kg, iv.), ending 5 minutes prior to either the PC ischemia or the injection of I-APNEA. At the end of 120 minutes of reperfusion, all animals were killed by an overdose of pentobarbital, and risk area and infarct size were measured.

Figure 5:
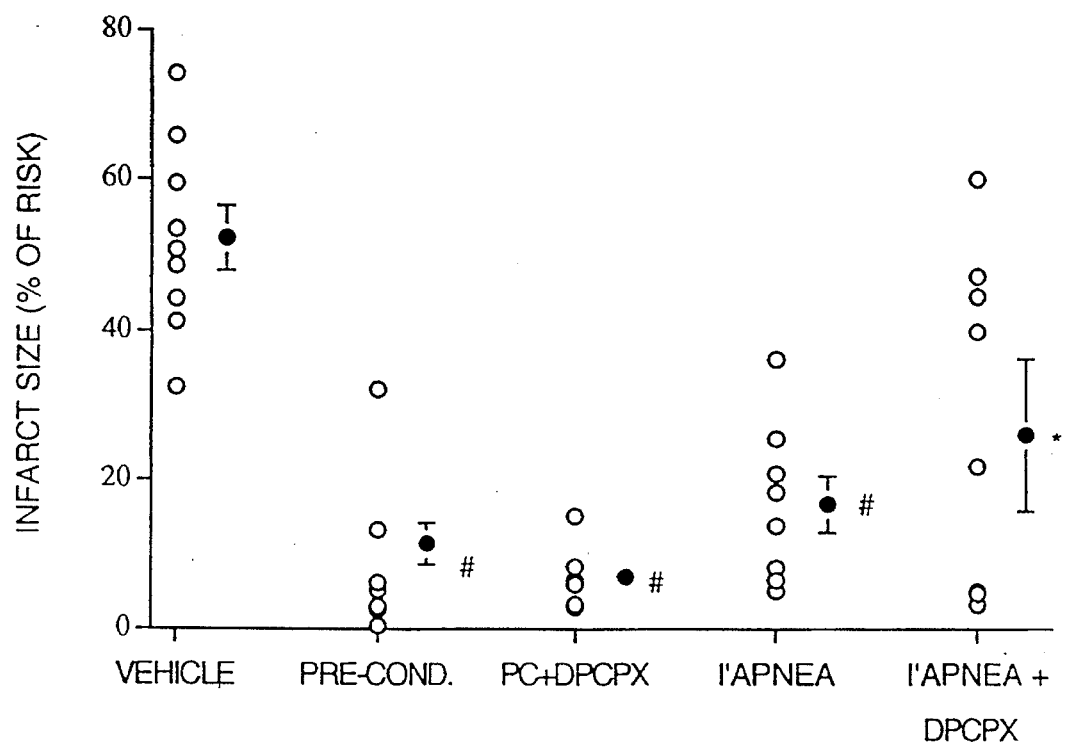
FIG. 5 is a graphical depiction of the comparison of the protective effects of preconditioning, preconditioning coupled with administration of an A1 antagonist (DPCPX), the administration of the A3 agonist APNEA and the coadministration of the adenosine A3 agonist APNEA and the A1 antagonist DPCPX.

Referring to FIG. 5, infarct size was 52±4.3% in untreated control rabbits. The infarct size was reduced to 9±4.1% by PC. I-APNEA reduced the infarct size to 17±3.8%. Pretreatment with the selective A1-receptor antagonist, DPCPX (0.5 mg/kg, IV), did not affect the reduction in infarct size with PC (7±1.8%) or I-APNEA (28±8.0%). DPCPX did abolish the bradycardia associated with activation of the A1 adenosine receptor and attenuated the fall in mean arterial pressure observed with administration of either I-APNEA (0.25 mg/kg) or the selective A1-receptor agonist, R-phenylisopropyladenosine (R-PIA, 1 mg/kg, iv.).

These results show that PC and I-APNEA reduce infarct size in anaesthetized rabbits by a non-A1 receptor dependent mechanism, and support the conclusion that activation of A3 receptors confers cardioprotection in intact, blood perfused rabbit hearts.

EXAMPLE 3

Adenosine $A_3$- Receptor Mediation of Preconditioning in Rabbit Heart.

The methods utilized in this example are identical to those described in Example 1. All hearts received 30 minutes of regional ischemia as described in Example 1. The control group (n=8) hearts received only 30 minutes of ischemia. Preconditioned (PC) hearts (n=10) received 5 minutes of global ischemia and 10 minutes of reperfusion prior to the regional ischemia. Adenosine (ADO) treated hearts (n=6) received 10 µM adenosine for 5 minutes prior to regional ischemia. APNEA treated hearts (n=6) received 65 µM APNEA for 5 minutes prior to regional ischemia. In groups receiving the nonselective adenosine blocker, 8-SPT, the blocker was included in the perfusate for 15 minutes at 100 µM starting 5 minutes before the exposure of ADO (ADO-SPT group, n=6), or APNEA (APNEA-SPT group, n=6 ) or 5 minutes before and after 5 minutes of preconditioning ischemia (PC-SPT group, n=5). The methods for groups ADO-DPCPX, (n=6), APNEA-DPCPX (n=6), and PC-DPCPX (n=5) were identical to the three SPT groups except that 200 nM DPCPX was substituted for the SPT. For the PC-BW group (n=5), the A3-receptor antagonist, BW A1433, [Linden J, et al., Molecular Pharmacology 44:524–532 (1993)], was administered at a dose of 200 nM in the perfusate for 5 minutes before and 5 minutes after PC ischemia.

Infarct size in control, untreated hearts averaged 32.2±1.5% of the risk area. PC with 5 minutes global ischemia and 10 minutes reperfusion prior to 30 minutes ischemia reduced infarct size to 8.8±2.3%. ADO and APNEA reduced infarct size to 11.4±2.3% and 12.6±2.2%, respectively. The non-selective adenosine receptor antagonist, 8-SPT, prevented the protection with PC (33.8±2.7%), ADO (29.8±3.7%) and APNEA (30.3±3.3%), but DPCPX, the selective A1-receptor antagonist, did not prevent the effects of the three interventions (15.6±7.8%, 14.4±2.8%, and 8.7±1.7%, respectively). However, BW A1433, a potent A3-receptor antagonist, completely blocked the protective effect of PC (26.2±3.2%).

The results with DPCPX show that cardioprotection with PC, ADO and APNEA is mediated via a non-A1 receptor mechanism. The results with BW A1433 show that the cardioprotection observed with PC in the rabbit heart is mediated by the A3-receptor.

EXAMPLE 4

Dose-response to the adenisine receptor agonist, APNEA, on infarct size in isolated rabbit hearts.

In this study, applicants examined the effects of varying the dosage of APNEA on myocardial infarct size in Langendorff buffer-perfused rabbit hearts subject to 30 minutes of regional ischemia and 2 hours reperfusion. The methods utilized in this example are identical to those described in Example 1.

Six groups of hearts were studied: control untreated hearts (n=10); APNEA 0.5 nM (n=6); APNEA 5 nM (n=6); APNEA 50 nM (n=6); APNEA 500 nM (n=6); and APNEA 500 nM+DPCPX 200 nM.(n=6) In all cases, APNEA (0.5–500 nM) was infused for 5 minutes, beginning 15 minutes prior to 30 minutes of ischemia. The regional ischemia was produced by occlusion of the coronary artery, followed by 120 minutes of reperfusion. The results are shown below in Table A.

TABLE A

| Treatment | n | Risk Area (% of LV) | Infarct Area (% of Risk) |
|---|---|---|---|
| Control | 10 | 44 ± 3 | 24 ± 1 |
| APNEA .5 nM | 6 | 45 ± 5 | 22 ± 5 |
| APNEA 5 nM | 6 | 57 ± 3 | 14 ± 3 |
| APNEA 50 nM | 6 | 52 ± 5 | 14 ± 3 |
| APNEA 500 nM | 6 | 45 ± 2 | 8 ± 1 |
| APNEA ± DPCPX | 6 | 53 ± 5 | 15 ± 5 |

At doses of 5, 50, and 500 nM, APNEA reduced infarct size, an effect which was not blocked by DPCPX. However, at a dose of 0.5 nM, APNEA had no effect on infarct size when compared to untreated control hearts.

In an additional group of 3 hearts that were not made ischemic, 500 nM APNEA was infused for 1 minute. This group of hearts was not paced to control heart rate, and the effects of APNEA on spontaneous heart rate and coronary flow were measured to determine the hemodynamic effects of APNEA.

APNEA (500 nM) had no effect on heart rate or coronary flow in non-ischemic hearts. In the three hearts studied, heart rate was 178±7 and 169±3 beats/min before and after APNEA, respectively. Coronary flow was 50±9 and 58±6 ml/min before and after APNEA, respectively.

These results show that APNEA reduces infarct size at doses of 5 nM and above, but that 0.5 nM APNEA is ineffective in reducing infarct size. The results further show that the reduction in infarct size with APNEA is mediated by a non-A1-adenosine receptor and the stimulation of the A3-receptor with APNEA results in no hemodynamic effects on coronary flow or heart rate.

EXAMPLE 5

A3 Adenosine Receptor Binding Assay

Chinese hamster ovary (CHO) cells, obtained from ATCC, expressing the cloned human A3 adenosine receptor [for example, 5 L cells or a mutagenized A3 adenosine receptor (e.g., A3K2)] were grown under standard cell culture conditions and harvested by mechanical agitation in cell culture medium. All further procedures were carried out at 4° C. The cells were disrupted using a Polytron and the resulting cell membranes collected by centrifugation at 50,000 g for 20 minutes. The pellet was suspended in 10 mM Tris-HCl buffer, pH 7.4, ($10^6$ cells/mL) using the Polytron and centrifuged at 50,000 g for 20 minutes. The resulting pellet was resuspended in 10 mM Tris-HCl buffer, pH 7.4, using the Polytron and centrifuged at 50,000 g for 20 minutes. The pellet was resuspended in 10 mM Tris-HCl buffer, pH 7.4 ($10^6$ cells/20 µL). A sample of the membrane suspension was taken for determination of the protein content by the method of Lowry, et al., (J. Biol. Chem. 193: 265–275, 1951).

For the binding assay, 50 µg of membrane protein were incubated with 0.4 nM [$^{125}$I]-aminobenzyladenosine (ABA, custom synthesized by DuPont:NEN; specific activity=2200 Ci/mmol) in 50 mM Tris-HCl buffer, pH 7.4, containing 5 mM $MgCl_2$ and 1 unit/mL adenosine deaminase in a total volume of 100 µL for 2 hours at room temperature. Membranes containing bound radioactivity were collected on Whatman GF/B filters using a Brandel Cell Harvester and washed 3 times with ice-cold 50 mM Tris-HCl buffer, pH 7.4. Radioactivity was quantified using a Beckman gamma counter. To determine receptor-bound radioactivity (specific binding), a parallel set of tubes containing 10 µM [$^{125}$I]-ABA, in addition to all other assay ingredients, was prepared in which radioactive bound non-specially to the membranes was measured. The specific binding was then calculated by subtracting this non-specific binding value from the total binding.

The specific binding of [$^{125}$I]ABA to the cell membranes of the A3K2 line was displaced by I-ABA in a concentration-dependent manner, with an $IC_{50}$ of 2 nM (FIG. 5). This indicates that the radiolabel binds to human A3 receptors expressed in these cells with high affinity.

TABLE 1

Some A1 and A2 receptor agonists and antagonists

| Abbreviation | Chemical Name |
|---|---|
| | $A_1$ agonists |
| R-PIA | (R)-N-(2-phenyl-1-methylethyl)adenosine |
| CPA | $N^6$-cyclopentyladenosine |
| CHA | $N^6$-cyclohexyladenosine |
| CCPA | 2-chloro-$N^6$-cyclopentyladenosine |
| 5-ENBA | $N^6$-endo-norborn-2-yladenosine |
| APNEA | N6-2-(4-amino-3-iodophenyl)ethyladenosine |
| ABA | $N^6$-(4-amino-3-iodobenzyl)adenosine |
| | $A_1$ antagonists |
| DPCPX | 1,3-dipropyl-8-cyclopentylxanthine |
| XAC | 8-(4-[({[(2-aminoethyl)amino]carbonyl}oxy]-phenyl}-1,3-dipropylxanthine |
| N-0861 | $N^6$-butyl-8-phenyladenine |
| KFM 19 | (±)-8-(3-oxocyclopentyl)-1,3-dipropylxanthine |
| BW-A844U | (3-[(4-amino)phenethyl]-8-cyclopentylexanthine |
| KF 15372 | 1,3-dipropyl-8-(dicyclopropylmethyl)xanthine |
| | $A_2$ agonists |
| CGS 21680 | 2-[4-(2-carboxylethyl)phenyl]ethylamino-5'-N-ethylcarboxamidoadenosine |
| CGS 22492 | 2-[(cyclohexylethyl)amino]adenosine |
| CGS 22989 | 2-[(cyclohexenyl)]amino]adenosine |
| CHEA | 2-(2-cyclohexylethoxy)adenosine |
| | $A_2$ antagonists |
| DATSX | 1,3-diallyl-8-(3,4,5-trim ethoxystyryl)-7-methylxanthine |
| DM TSX | 8-(3,4,5-trimethoxystyryl)-1,3,7-trimethylxanthine |

We claim:

1. A method for reducing ischemic damage to an organ having A3 adenosine receptors for those patients at risk of ischemic damage, comprising the step of:

administering to the organ a therapeutic amount of an agonist to the A3 adenosine receptor, wherein the A3 adenosine receptor agonist is administered orally.

2. A method as in claim 1 wherein the A3 adenosine receptor agonist is APNEA.

3. A method as in claim 1 wherein the organ having A3 adenosine receptors is the heart.

4. A method as in claim 1 further comprising the step of administering an antagonist to A1 adenosine receptors, wherein the A1 adenosine receptor antagonist is administered orally.

5. A method as in claim 4 wherein the A1 adenosine receptor antagonist is administered to the organ having A3 adenosine receptors before the A3 adenosine receptor agonist is administered.

6. A method as in claim 4 wherein the organ is the heart.

7. A method as in claim 4 wherein the antagonist to A1 adenosine receptors is selected from the group consisting of DPCPX, XAC, BW-A844U, N-0861, KF 15372 and KFM 19.

8. A method as in claim 1 wherein the A3 adenosine receptor agonist has a selectivity for the A3 adenosine receptor of at least about 10:1 over A1 and A2 adenosine receptors.

9. A method as in claim 1 wherein the A3 adenosine receptor agonist has a selectivity for the A3 adenosine receptor of at least about 100:1 over A1 and A2 adenosine receptors.

10. A method as in claim 1 wherein the A3 adenosine receptor agonist is administered prophylactically.

11. A method for preconditioning tissues and organs having A3 adenosine receptors to protect the tissues and organs from ischemic damage for patients in which preconditioning would be beneficial, comprising the step of:

administering to the patient an ischemic damage reducing amount of an agonist to the A3 adenosine receptor using an administration technique selected from the group consisting of intravenous administration, oral administration and perfusion of the tissues and organs.

12. A method as in claim 11 wherein the agonist to the A3 adenosine receptor is selected from the group consisting of $N^6$-(2-(4-aminophenyl)ethyl)adenosine (APNEA), $N^6$-2-(4-amino-3-iodophenyl)ethyladenosine (I-APNEA), 5'-N-ethylcarboxamidoadenosine (NECA), $N^6$-benzyladenosine-5'-N-methyluronamide, $N^6$-(3-bromobenzyl)-adenosine-5'-N-methyluronamide, $N^6$-(3-iodobenzyl)adenosine-5'-N-methyluronamide, and $N^6$-(3-chlorobenzyl)adenosine-5'-N-methyluronamide.

13. A method as in claim 11 wherein the organ having A3 adenosine receptors is the heart.

14. A method as in claim 13 wherein the A3 adenosine receptor agonist is administered by perfusing the heart during surgery.

15. A method as in claim 13 wherein the A3 adenosine receptor agonist is intravenously administered before and during surgery.

16. A method as in claim 11 wherein the organ having A3 adenosine receptors is the brain.

17. A method as in claim 16 wherein the A3 adenosine receptor agonist is administered during surgery.

18. A method as in claim 11 wherein the A3 adenosine receptor agonist has a selectivity for the A3 adenosine receptor of at least about 10:1 over A1 adenosine receptors.

19. A method as in claim 18 wherein the selectivity is 100:1.

20. A method as in claim 11 wherein the A3 adenosine receptor agonist has a selectivity for the A3 adenosine receptor of at least about 10:1 over A2 adenosine receptors.

21. A method as in claim 20 wherein the selectivity is 100:1.

22. A method for preconditioning tissues and organs having A1 and A3 adenosine receptors to protect the organ from ischemic damage for patients in need of preconditioning, comprising the steps of:

administering to the patient an antagonist to the A1 adenosine receptor, wherein the amount of A1 adenosine receptor antagonist administered to the patient is sufficient to prevent stimulation of the A1 adenosine receptors that is adverse to the patient; and administering to the patient an ischemic damage reducing amount of an agonist to the A3 adenosine receptor, wherein the A1 adenosine receptor antagonist and the A3 adenosine receptor agonist are administered orally, intravenously or by perfusion of the tissues and organs.

23. A method as in claim 22 wherein the A1 adenosine receptor antagonist and the A3 adenosine receptor agonist are administered to protect the heart from ischemic damage.

24. A method as in claim 22 wherein the A1 adenosine receptor antagonist and the A3 adenosine receptor agonist are administered to protect the brain from ischemic damage.

25. A method as in claim 22 wherein the A3 adenosine receptor agonist is selected from the group consisting of $N^6$-(2-(4-aminophenyl)ethyl)adenosine (APNEA), $N^6$-2-(4-amino-3-iodophenyl)ethyladenosine (I-APNEA), 5'-N-ethylcarboxamidoadenosine (NECA), $N^6$-benzyladenosine-5'-N-methyluronamide, $N^6$-(3-bromobenzyl)adenosine-5'-N-methyluronamide, $N^6$-(3-iodobenzyl)adenosine-5'-N-methyluronamide, and $N^6$-(3-chlorobenzyl)adenosine-5'-N-methyluronamide.

26. A method as in claim 22 wherein the A1 adenosine receptor antagonist is selected from the group consisting of DPCPX, XAC, BW-A844U, N-0861, KF 15372 and KFM 19.

27. A method as in claim 22 further comprising the step of administering to tissues and organs having A2 adenosine receptors an antagonist to the A2 adenosine receptor, wherein the A2 adenosine receptor antagonist is administered orally, intravenously or by perfusion of the tissues and organs.

28. A method as in claim 27 wherein the A2 adenosine receptor antagonist is selected from the group consisting of DATSX and DM TSX.

29. A method for protecting an organ having A3 adenosine receptors for patients in need thereof, comprising the step of:

administering an A3 adenosine receptor agonist to the patient using an administration technique selected from the group consisting of oral, intravenous and perfusion.

30. A method as in claim 29 wherein the organ having A3 adenosine receptors is the heart.

31. A method as in claim 30 wherein the A3 adenosine receptor agonist is administered during surgery.

32. A method as in claim 31 wherein the A3 adenosine receptor agonist has a selectivity of 10:1 over A1 and A2 adenosine receptors.

33. A method as in claim 29 wherein the organ having A3 adenosine receptors is the brain.

34. A method as in claim 29 further comprising the step of administering to tissues and organs having A2 adenosine receptors an antagonist to the A2 adenosine receptor, wherein the A2 adenosine receptor antagonist is administered orally, intravenously or by perfusion of the tissues and organs.

35. A method as in claim 34 wherein the A2 adenosine receptor antagonist is selected from the group consisting of DATSX and DM TSX.

* * * * *